United States Patent [19]

Vaartstra

[11] Patent Number: 5,659,057
[45] Date of Patent: Aug. 19, 1997

[54] FIVE- AND SIX-COORDINATE PRECURSORS FOR TITANIUM NITRIDE DEPOSITION

[75] Inventor: Brian A. Vaartstra, Nampa, Id.

[73] Assignee: Micron Technology, Inc., Boise, Id.

[21] Appl. No.: 599,565

[22] Filed: Feb. 9, 1996

[51] Int. Cl.$^6$ ................................................ C07F 7/28
[52] U.S. Cl. ...................... 556/51; 427/419.7; 427/590
[58] Field of Search .................. 556/51; 427/419.7, 427/590

[56] References Cited

U.S. PATENT DOCUMENTS

| | | | |
|---|---|---|---|
| 4,340,617 | 7/1982 | Deutsch et al. | 427/53 |
| 4,713,258 | 12/1987 | Umemura | 427/35 |
| 4,721,631 | 1/1988 | Endo et al. | 427/66 |
| 4,868,005 | 9/1989 | Ehrlich et al. | 427/531 |
| 4,876,112 | 10/1989 | Kaito et al. | 427/38 |
| 4,923,717 | 5/1990 | Gladfelter et al. | 427/252 |
| 5,005,519 | 4/1991 | Egermeier et al. | 118/722 |
| 5,022,905 | 6/1991 | Grundy et al. | 65/60 |
| 5,139,825 | 8/1992 | Gordon et al. | 427/255.2 |
| 5,151,009 | 9/1992 | Gladfelter et al. | 566/27 |
| 5,227,334 | 7/1993 | Sandhu | 437/190 |
| 5,254,499 | 10/1993 | Sandhu et al. | 437/192 |
| 5,300,321 | 4/1994 | Nakano et al. | 427/248 |
| 5,314,727 | 5/1994 | McCormick et al. | 427/584 |
| 5,348,587 | 9/1994 | Eichman et al. | 118/723 |
| 5,378,501 | 1/1995 | Foster et al. | 427/255.2 |
| 5,464,656 | 11/1995 | Verkade | 427/248.1 |

OTHER PUBLICATIONS

Fix, et al., "Chemistry of Materials", *Chemical Vapor Deposition of Vanadium, Niobium, and Tantalum Nitride Thin Films*, pp. 614–619, (May 1993).

L. P. Herman, *Chem. Rev.*, 89, *1323 (no month)*, pp. 1346–1349.

David M. Hoffman, "Polyheron: vol. 13 No. 8", *Chemical Vapour Deposition of Nitride Thin Films*, Department of Chemistry, University of Houston, TX, pp. 1160–1179, (1994).

C. E. Morosanu, "Thin Films by Chemical Vapor Deposition", *Elsevier, N.Y.* at pp. 42–54, 460–475 (1990).

G. Sandhu, et al., "Metalorganic Chemical Vapor Deposition of TiN Films for Advanced Metallization", (Nov. 1992).

X. Sun, et al., "Ti–Si–N Diffusion Barriers for Al & Cu Metallizations", California Institute of Technology.

Louis E. Toth, "Transition Metal Carbides and Nitrides", J.L. Margrave, ed., vol. 7, Academic Press, NY (1971), Entire Book.

Travis, et al., "A Scalable Submicron Contact Technology Using Conformal LPCVD TiN", *IEDM Technical Digest*, pp. 47–49, (1990).

Simon R Drake, et al., "Titanium Amide Molecular Precursors for Titanium Nitride", *Polyhedron*, 13(2), pp. 181–186, (Jan. 1994).

J. H. Liao, et al., "Experimental and Simulation Studies of Atmospheric Pressure Chemical Vapor Deposition of Titanium Nitride From Tetrakis–Dimethylaminotitanium and Ammonia", *Conference Proceedings ULSI-X*, Materials Research Society, pp. 231–237, (1995).

*Primary Examiner*—Porfirio Nazario-Gonzalez
*Attorney, Agent, or Firm*—Schwegman, Lundberg, Woessner & Kluth, P.A.

[57] ABSTRACT

Improved precursors for use in chemical vapor deposition of thin films of titanium-based materials are provided, which are either 5- or 6-coordinate and thus sterically saturated and protected from attack of the coreactant in the gas phase. Specific precursors have the formula $Ti[N(R^1)(R^2)]_x[(R^3)N-C(R^4)(R^5)-C(R^6)(R^7)-N(R^8)(R^9)]_y$, wherein each of $R^1$, $R^2$, $R^3$, $R^8$ and $R^9$ are $(C_1-C_4)$ alkyl, each of $R^4$, $R^5$, $R^6$, and $R^7$ are each H or $(C_1-C_4)$ alkyl and x and y are 1–3. The thin films produced include titanium nitride and amorphous titanium-silicon-nitride.

6 Claims, 1 Drawing Sheet

FIVE- AND SIX-COORDINATE PRECURSORS FOR TITANIUM NITRIDE DEPOSITION

BACKGROUND OF THE INVENTION

Titanium nitride (TiN) is a technologically important transition metal nitride. Hoffman, *Polyhedron*, 13, 1169 (1994). It is a better electrical conductor than is titanium metal and its optical properties resemble those of gold. Toth, *Transition Metal Carbides and Nitrides*, J. L. Margrave, ed., vol. 7, Academic Press, New York (1971). Titanium nitride is also harder than all elemental metals and sapphire and almost as hard as diamond, having a melting point of about 3000° C. Additionally, TiN is a low temperature superconductor.

TiN films have many potential applications because of their unique combination of properties. Fix et al., *Chem. Mater.*, 5, 614 (1993). They are used, for example, as wear-resistant, friction-reducing coatings on machine tools and as gold-colored decorative coatings. Their optical properties also make them useful as wavelength selective transparent films, and in particular as solar control coatings on windows in warm weather climates. In microelectric devices, TiN films can be used a low resistance contacts and as diffusion barriers in interconnect metallization schemes.

Inorganic thin films such as TiN are commonly prepared by chemical vapor deposition (CVD). In CVD, a heat decomposable volatile compound (often an organometallic compound), or "precursor", is contacted with a substrate which has been heated to a temperature above the decomposition temperature of the compound. A coating forms on the substrate which may be a metal, metal mixture or alloy, ceramic, metal compound or mixture thereof, depending on the choice of precursor and reaction conditions. Optionally, a volatile reactant gas is employed alone or as a part of the carrier gas to adjust the composition of the final coating. The desirable characteristics of CVD as a thin film formation method include its ability to produce a thin film with good step coverage on a substrate having projections, the ability to readily control the composition of the thin film, and the ability to form a thin film without contamination of, or damage to, the substrate.

However, known CVD processes for manufacturing TiN films suffer many limitations, primarily due to the precursors employed. For example, although it is feasible to carry out CVD employing metalorganic precursors (e.g., dialkylamino-derivatives of titanium [Ti(NR$_2$)$_4$]) to produce TiN films, the carbon content of the resulting TiN film is typically unacceptably high. This problem can be overcome with the use of ammonia in the carrier gas, but this in turn creates problems with gas phase prereactions, with the consequence that the resulting films have poor conformality. Therefore, a need exists for an improved titanium precursor to be used in a CVD process for manufacturing TiN films.

SUMMARY OF THE INVENTION

The present invention provides a novel precursor for use in the chemical vapor deposition of TiN or amorphous Ti-Si-N films. The precursor of the present invention is preferably a 5- or 6-coordinate dialkylamino complex of titanium of the general formula (I):

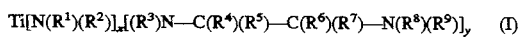

wherein each of R$^1$, R$^2$, R$^3$, R$^8$ and R$^9$ are (C$_1$–C$_4$) alkyl, and R$^4$, R$^5$, R$^6$, and R$^7$ are each H or (C$_1$–C$_4$) alkyl; and wherein x and y are each 1–3. More preferably, the precursors have the formula (II):

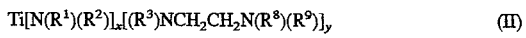

wherein R$^1$, R$^2$, R$^3$, R$^8$, R$^9$, x and y are as previously defined. Most preferably, the precursor is either bis (dimethylamino)-bis(N,N,N'-trimethylethylenediamino) titanium, i.e., each of R$^1$, R$^2$, R$^3$, R$^8$ and R$^9$ are each CH$_3$, x is 2 and y is 2 (a six-coordinate complex) or tris (dimethylamino)-mono((N,N,N'-trimethylethylenediamino) titanium, i.e., each of R$^1$, R$^2$, R$^3$, R$^8$ and R$^9$ are each CH$_3$, x is 3 and y is 1 (a five-coordinate species). As used herein, with respect to the compounds of formula (I) or formula (II), the term "alkyl" includes branched or straight-chain alkyl, optionally comprising 1–2 double bonds and wherein, optionally, the carbon chain is interrupted by 1–3, preferably by about 1–2N, non-peroxide O, Si or mixtures thereof, e.g., by N(R$^4$) or Si(R$^4$)$_2$. In the complexes of formula I or II, the diamino ligand can act as a mono- or bi-functional chelator, preferably, it acts as a bifunctional chelator of titanium, i.e., y is 1–2. Preferably, the precursors are liquids or volatile solids. The precursors of the present invention are suitable for ultralarge scale integrated (ULSI) circuit applications, in which gas-phase prereaction of gases is limited by use of precursor complexes of titanium specifically engineered to inhibit reactivity with other gas phase molecules.

The synthetic procedure followed to synthesize a preferred precursor of the present invention is outlined in Scheme (1) below, and yields tris(dimethylamino)-mono( (N,N,N'-trimethylethylenediamino)titanium in good yields:

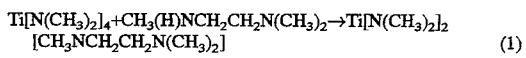

The process used to deposit the compounds of the present invention is disclosed in the co-pending, commonly-assigned U.S. patent application Ser. No. 08/764,858, filed Dec. 13, 1996, which is a divisional application U.S. patent application Ser. No. 08/600,780, filed Feb. 9, 1996, now allowed.

DETAILED DESCRIPTION OF THE INVENTION

Figure 1:
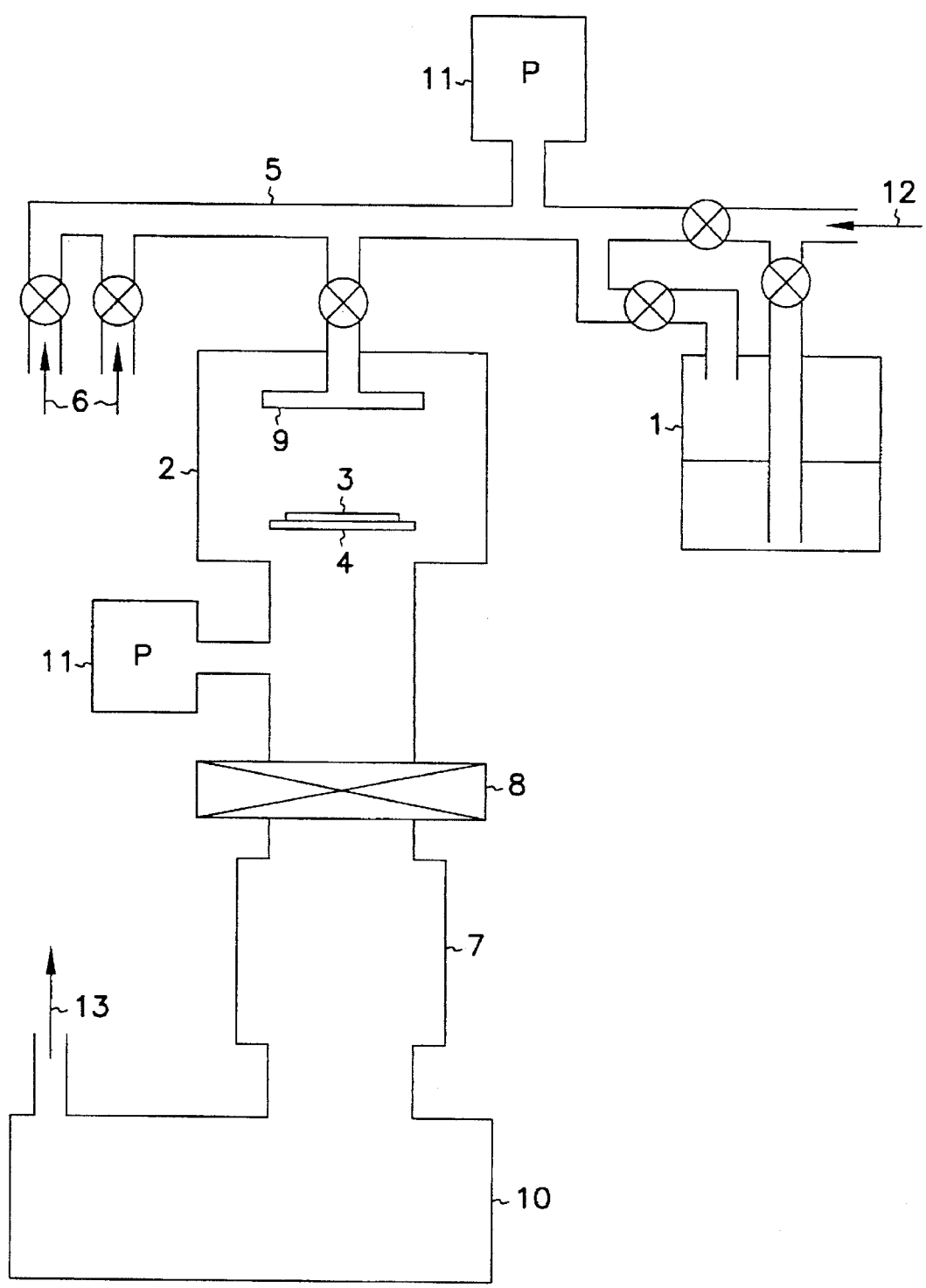
FIG. 1 is a schematic representation of a chemical vapor deposition apparatus useful in the utilization of the precursors of the present invention.

Applicant has made the surprising discovery that by sterically saturating the metal center of a titanium precursor molecule, i.e., by making it either 5- or 6-coordinate, precoordination of a reactant gas, such as ammonia, is inhibited.

The present invention is thus directed to improved precursors for use in the chemical vapor deposition of titanium-containing thin films.

A. Chemical Vapor Deposition

This invention broadly relates to novel precursors for use in the CVD method of preparing TiN films, which when used in the CVD process, result in the deposition of high quality TiN films, at low temperature on a wide variety of substrates. As described by C. E. Morosanu in "Thin Films by Chemical Vapor Deposition," Elsevier, N.Y. (1990) at pages 42–54, CVD is classified into various types in accordance with the heating method, gas pressure, and/or chemical reaction. For example, conventional CVD methods include (a) cold wall type CVD, in which only a deposition substrate is heated; (b) hot wall type CVD, in which an entire reaction chamber is heated; (c) atmospheric CVD, in which reaction occurs at a pressure of about one atmosphere; (d) low-pressure CVD in which reaction occurs at pressures from about $10^{-1}$ to 100 torr; (e) electron-beam assisted CVD and ion-beam assisted CVD in which the energy from an electron-beam or an ion-beam directed towards the substrate provides the energy for decomposition of the precursor; (f) plasma assisted CVD and photo-assisted CVD in which the energy from a plasma or a light source activates the precursor to allow depositions at reduced substrate temperatures; and (g) laser assisted CVD wherein laser light is used to heat the substrate or to effect photolytic reactions in the precursor gas.

The laser CVD method is thoroughly discussed by I. P. Herman, *Chemical Reviews.*, 89, 1323 (1989). Pyrolytic depositions are discussed on pages 1346–8 and photolytic depositions are discussed on pages 1348–9 of this review. An example of ion-beam assisted CVD is found in U.S. Pat. No. 4,876,112. An example of photo-assisted CVD is found in U.S. Pat. No. 5,005,519. An example of laser assisted CVD is found in U.S. Pat. No. 4,340,617. An example of electron-beam assisted CVD is found in U.S. Pat. No. 4,713,258. An example of plasma assisted CVD is found in U.S. Pat. No. 4,721,631. Examples of low pressure CVD and hot wall CVD are found in U.S. Pat. No. 4,923,717. An example of atmospheric CVD is found in U.S. Pat. No. 5,022,905. Examples of low pressure CVD and cold wall CVD are found in U.S. Pat. No. 4,868,005. Heating of substrates in a cold wall CVD reactor may be accomplished by several methods including the use of hot stages or induction heating.

Broadly, thermal CVD includes any type of apparatus in which the substrate and/or the gaseous precursor is heated and could include standard thermal reactors such as cold wall/hot substrate reactors and hot wall type reactors, as well as radiation beam reactors in which a beam (such as a laser beam) is used to heat the substrate and/or to decompose gaseous precursor.

B. The CVD Process

In a typical CVD process, the substrate on which deposition is to occur is placed in a reaction chamber, and is heated to a temperature sufficient to cause the decomposition of vapors of the precursor complex. When these vapors are introduced into the reaction chamber and transported to the vicinity of the substrate, they will decompose thereon to deposit a film containing the metal, and selected elements from the precursor or reactant gas.

In a thermal reactor CVD system, it is preferable that the decomposition reaction occur at the substrate, and for this reason it is preferable to heat the substrate to a temperature in excess of the decomposition temperature of the precursor. In a radiation beam induced CVD technique, the radiation (such as an ion beam) is preferably used to heat the substrate so that decomposition of the precursor occurs at the substrate.

These CVD processes can be used to provide blanket deposition of titanium nitride films on substrates, as well as to provide deposition of these films on selected areas of the substrate, i.e., by use of a masking material, such as a resist material. Additionally, selected area depositions may be accomplished by energy beam assisted CVD where a beam of energy, such as an ion beam selectively heats small portions of the substrate.

Any CVD apparatus design may be used when depositing TiN films from the precursors of the present invention including hot wall reactors, cold wall reactors, radiation beam assisted reactors, plasma assisted reactors, and the like. For blanket depositions, a cold wall-hot substrate reactor may sometimes be preferred as this design is efficient in regards to precursor consumption. For selected area depositions, a radiation beam assisted reactor may be preferred as the radiation beam may be used to "write" metal containing films onto small areas of the substrate.

As described in Example 3, hereinbelow, the growth of TiN films is conducted with an inert carrier gas, e.g., helium, argon and a reactant gas such as ammonia, nitrogen trifluoride or hydrazine optionally mixed with one or more of hydrogen, nitrogen, argon or helium, under 0.01–10.0 torr in a standard CVD reactor. Such a reactor is depicted in FIG. 1.

As shown in FIG. 1, the precursor is contained in a reservoir (1) at one end of a reaction chamber (2). The precursor is exposed to a vacuum by opening a valve (8). The vacuum can be provided by a suitable vacuum pump (7) and/or forepump (10) (with exhaust means (13)) positioned at the opposite end of the reaction chamber (2). The precursor is vaporized and carried to the reaction chamber (2) using a carrier gas (12), which is bubbled through the precursor. The precursor vapor then passes through warmed connecting lines (5) into a reaction chamber (2) that contains one or more units of the substrate (3). The substrate, e.g., wafers of Si<100>, are preferably held in horizontal position on top of a heater (4). Preferably, the heater (4) maintains the temperature of the substrate (3) at about 200°–800° C. during the deposition process, most preferably at about 300°–400° C. The system also includes a reservoir containing the reactant gas (6). The precursor vapor stream and a reactant gas are combined either prior to (i.e., in the connecting lines (5)) or inside the reaction chamber (2). The combined vapor stream is then delivered into the reaction chamber (2) through a showerhead (9) where the heat of the substrate (3) is sufficient to decompose the precursor vapor so as to deposit a Ti-containing film. The system may further comprise auxiliary pumps (11).

Generally, vacuum systems are used for CVD of titanium-containing films. There is no criticality with respect to the pressure in the system, operating pressures of 1 to 100 mtorr have been used in the absence of carrier gas and higher or lower pressures are also acceptable, i.e., up to about atmospheric pressure. These pressures are largely determined by the pumping speed of the vacuum equipment, the vapor pressure of the precursor complex, and inert carrier gases can be added to increase the total pressure.

It is often desirable to use a carrier gas in a CVD process, which is passed through or over a solid or liquid precursor. In this case, an inert carrier gas is used, e.g., argon or helium. The vapor stream comprising the precursor and the inert carrier gas is then mixed, either in the transfer lines or in the reaction chamber, with a reactant gas such as ammonia, nitrogen, hydrazine, hydrogen, water, nitrogen trifluoride, silane, hydrogen sulfide, and the like. When carrier gases are used pressures may range from about 0.01 torr to about 760 torr (atmospheric pressure) and are more typically in the range of 0.1 to 300 torr. However, these pressures do not appear to be highly critical to the deposition of the films.

The precursor is generally maintained at a constant temperature during the vaporization process for ease of handling; however, this is not critical. the temperature is generally below the respective decomposition temperature, but at a temperature such that it is sufficiently capable of being volatilized in the process of chemical vapor deposition.

C. Substrates

Any type of substrate can be used in CVD, including metals, graphite, semiconductors, insulators, ceramics and the like as long as the substrate is not substantially deteriorated under the deposition conditions. Furthermore, suitable substrates may have one or more deposit layers already present. Such substrates include, but are not limited to, silicon, tin oxide, gallium arsenide (GaAs), silica, glass, alumina, zirconia, as well as polyimide, polymethylmethacrylate, polystyrene and other synthetic polymers. More specifically, substrates useful for electronic device applications include Si<100>, Si<311>, Si<111>, Si<110>, GaAs<110>, GaAs<111> and GaAs<311>. Prior to initiating CVD, the substrates, such as Si<100> wafers, can be pre-cleaned by the standard means of sequential soaking in baths of tetrachloroethane, methanol, distilled water, dilute hydrofluoric acid, and distilled water.

CVD can be used to deposit metals on either planar substrate surfaces or as continuous layers into recesses, trenches, and vias, and over stepped surfaces, such as those which are topologically microstructured. The substrate can be of any desired shape, either regular or irregular. Thus, the substrate can be a rectangular solid or other solid characterized by flat exterior surfaces. Cylindrical surfaces, such as rods and wires, can also be coated according to this invention. Spherical surfaces and other curves surfaces can also be coated. The substrate can even be particulate and/or be hollow, as for example, a tube or a hollow or porous sphere or irregular particle having openings to the exterior.

D. The Precursors of the Present Invention

The present invention recognizes that conformal TiN or TiSiN films can be achieved only if film deposition rates are limited by the reaction rate rather than the rate of delivery of the reactants. This prerequisite requires that a relatively low substrate temperature and a controlled rate of reaction of the reactant gas and the titanium-containing precursor be employed. The precursors of the present invention have thus been specifically engineered to inhibit their reactivity with the reactant gas. Specifically, the precursors of the present invention contain 5- or 6-coordinate molecular species of titanium which are sterically saturated and thus, protected from attack in the gas phase. By virtue of this specifically engineered property, the precursors of the present invention will have activation energies which can only be reached at the substrate surface, allowing the deposition process to proceed at the desired rate.

Specifically, the precursors of the present invention are of the general formula Ti[N(R$^1$)(R$^2$)]$_x$[(R$^3$)N—C(R$^4$)(R$^5$)—C(R$^6$)(R$^7$)—N(R$^8$)(R$^9$)]$_y$ wherein each of R$^1$, R$^2$, R$^3$, R$^8$ and R$^9$ are (C$_1$—C$_4$) alkyl, each of R$^4$, R$^5$, R$^6$, and R$^7$ are each H or (C$_1$–C$_4$) alkyl and x and y are each 1–3. Preferred precursors useful for the deposition of TiN include bis (dimethylamino)-bis-(N,N,N'-trimethylethylenediamino) titanium, i.e., each of R$^1$, R$^2$, R$^3$, R$^8$ and R$^9$ are each CH$_3$, x is 2 and y is 2 and tris(dimethylamino)-mono((N,N,N'-trimethylethylenediamino)titanium, i.e., each of R$^1$, R$^2$, R$^3$, R$^8$ and R$^9$ are each CH$_3$, x is 3 and y is 1.

The examples hereinbelow describe preparation of a preferred precursor complex. The volatility of the precursor produced in Examples 1–2 indicates that the material is suitable for chemical vapor deposition of titanium-based thin films in ULSI applications. The specific precursor compound produced is likely to be the most volatile of the any of the compounds of the class. It is believed that this specific compound can be used for chemical vapor deposition of titanium-based materials such as (but not limited to) titanium nitride and titanium silicide. Also, use of the compounds should reduce difficulties in gas phase prereaction between silane and Ti(NR$_2$)$_4$ complexes when amorphous titanium-silicon-nitrogen (Ti—Si—N) diffusion barrier layers are employed for aluminum and copper metallizations. In either case, process knowledge currently within the skill of the art may be employed to design a complete chemical vapor deposition process using the compounds produced in the examples hereinbelow. Specifically, Example 3 hereinbelow demonstrates that the precursors of the present invention have a blend of physical and chemical properties that render them highly useful as liquid precursors for titanium nitride films in chemical vapor deposition processes.

The invention will be further described by reference to the following detailed examples.

EXAMPLE 1

A Schlenk flask was dried and purged with argon, then charged with 10.0 ml (9.6 g, 0.043 mol) of TDMAT that had been cooled in an ice bath. To this, 10.88 ml of N,N,N-trimethylethylenediamine was added dropwise. The mixture became orange-red slowly and was stirred overnight. The next day, a miniature distillation apparatus was attached and distillation begun. The first fraction was collected at approximately 40° C. and 90 mTorr and was identified to be a few milliliters of TDMAT. The next fraction was a red compound collected between 80°–95° C. One week later, the red compound was further purified by distilling off any remaining TDMAT. A sample was analyzed by nuclear magnetic resonance by a commercial laboratory and confirmed to be essentially pure Ti[N(CH$_3$)$_2$]$_3$[(CH$_3$)NCH$_2$CH$_2$N(CH$_3$)$_2$].

EXAMPLE 2

A dry, argon-purged vessel was charged with 10.0 mL (9.6 g, 0.043 mol) of tetrakis(dimethylamino)-titanium (TDMAT). To this was added 10.88 mL (0.086 mol) of N,N,N'-trimethylethylenediamine (Aldrich Chemical Co.). The mixture became darker orange during the addition.

After 72 hours the crude mixture was distilled at reduced pressure under an argon atmosphere. The first fraction was taken off at 30° C. (60 mtorr) corresponding to the boiling point of TDMAT.

A second, major fraction was taken off at 94° C. (75 mtorr), and found to be a dark red compound which crystallized at room temperature, but readily melted above 30° C. This second fraction was distilled a second time, withdrawing the fraction which came off between 90° and 94° C. (65 mtorr). The compound was identified by its NMR spectrum (Spectral Data Services Inc., Champaign, Ill.) in benzene-d$_6$: 3.16 ppm (s, 18H), 1.95 ppm (s, 6H), 3.20 ppm (s, 3H), 3.12 ppm (tr, 2H), 2.50 ppm (tr, 2H). Integration of the peaks was consistent with the formulation Ti[N(CH$_3$)$_2$]$_3$ [N(CH$_3$)CH$_2$CH$_2$N(CH$_3$)$_2$].

EXAMPLE 3

A reservoir was charged with tris(dimethylamino) (N,N, N'-trimethyl ethylenediamino)titanium and maintained at 50° C. The vapor was delivered to the reaction chamber using a carrier gas (helium at 5 sccm) bubbled through the precursor. The lines connecting the reservoir to the reaction chamber were warmed to 60° C. The substrate (1"×1.5" silicon wafer with silicon oxide deposited on it or a portion of processed wafer with 5:1 aspect ratio contact holes) was maintained at 350° C. (measured by a thermocouple in contact with the substrate surface) inside the reaction chamber, which was held at a pressure of 0.5 torr. A reactant gas mixture containing 50 sccm N$_2$ and 50 sccm ammonia was introduced to the precursor vapor, upstream of the reaction chamber. The precursor vapor was delivered for 2.5 minutes.

The final TiN growth rate was determined to be 3.5 angstroms per second. The mean thickness was determined to be 520 angstroms using a Tencor P-1 Long Scan proffer. The sheet resistance was found to have a mean value of 1800 microohm-cm using a Prometrix Omnimap RS-50e. XPS was used to determine the composition of the film, which was 48 atom % titanium, 32 atom % nitrogen, 5 atom % carbon and 15 atom % oxygen. Scanning electron microscopy (SEM) was used to determine step coverage for a 2 micron×0.4 micron contact hole (5:1 aspect ratio). The ratio of coverage on the lower sidewall to that on the upper sidewall was 80%.

All patents and publications are incorporated by reference herein, as though individually incorporated by reference. While only certain preferred embodiments of this invention have been shown and described by way of illustration, many modifications will occur to those skilled in the art and it is, therefore, desired that it be understood that this is intended herein to cover all such modifications that fall within the spirit and scope of this invention.

What is claimed is:

1. A compound of formula (I):

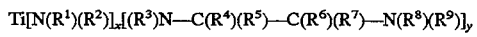

wherein (a) each of $R^1$, $R^2$, $R^3$, $R^8$ and $R^9$ are $(C_1-C_4)$ alkyl;
(b) each of $R^4$, $R^5$, $R^6$, and $R^7$ are each H or $(C_1-C_4)$ alkyl; and
(c) each of x and y are 1–3.

2. The compound of claim 1 wherein $R^4$, $R^5$, $R^6$, and $R^7$ are each H and wherein $R^1$, $R^2$, $R^3$, $R^8$ and $R^9$ are $(C_1-C_4)$ alkyl.

3. The compound of claim 2 wherein $R^1$, $R^2$, $R^3$, $R^8$ and $R^9$ are each $CH_3$.

4. The compound of claim 3 wherein x is 2 and y is 2.

5. The compound of claim 3 wherein x is 3 and y is 1.

6. A compound of formula (I)

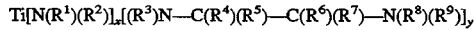

wherein (a) each of $R^1$, $R^2$, $R^3$, $R^8$ and $R^9$ are $(C_1-C_4)$ alkyl;
(b) cash of $R^4$, $R^5$, $R^6$, and $R^7$ are each H or $(C_1-C_4)$ alkyl;
(c) each of x and y are 1–3; and
(d) wherein, optionally, the carbon chain of each $(C_1-C_4)$ alkyl is interrupted by 1–3N, non-peroxide O, Si or mixtures thereof.

* * * * *